United States Patent [19]

Magee, Jr.

[11] Patent Number: 5,305,658
[45] Date of Patent: Apr. 26, 1994

[54] CAPSULE TRANSFER DEVICE

[75] Inventor: Leo J. Magee, Jr., Cohoes, N.Y.

[73] Assignee: Sterling Winthrop Inc., Malvern, Pa.

[21] Appl. No.: 908,124

[22] Filed: Jul. 1, 1992

[51] Int. Cl.⁵ .................................................. B65D 83/76
[52] U.S. Cl. ................................... 73/864.82; 206/532
[58] Field of Search ................. 73/864.82, 863, 864.91, 73/864.87; 206/532

[56] References Cited

U.S. PATENT DOCUMENTS

| Re. 29,656 | 6/1978 | Chittenden et al. | 604/413 |
|---|---|---|---|
| 1,383,270 | 6/1921 | Henning | 222/83 |
| 1,826,809 | 10/1931 | Metz | 206/532 X |
| 2,753,868 | 7/1956 | Seemar | 206/571 X |
| 2,773,591 | 12/1956 | Jensen | 206/221 X |
| 3,002,387 | 10/1961 | Micheletti | |
| 3,421,857 | 1/1969 | Reichle et al. | 73/864.82 X |
| 3,458,699 | 7/1969 | Padtra | 73/864.82 X |
| 3,783,694 | 1/1974 | Otte et al. | |
| 4,113,097 | 9/1978 | Finn | 206/528 |
| 4,192,309 | 3/1980 | Paulsen | |
| 4,578,244 | 3/1986 | Cosgrove et al. | 422/102 X |
| 4,793,493 | 12/1988 | Makiej, Jr. | 206/531 X |
| 4,821,586 | 4/1989 | Scordato et al. | 73/864.18 |
| 4,975,015 | 12/1990 | Harding | 206/532 X |
| 5,046,627 | 9/1991 | Hansen | 206/532 X |

FOREIGN PATENT DOCUMENTS

| 1286445 | 1/1969 | Fed. Rep. of Germany | 206/532 |
|---|---|---|---|
| 2282634 | 3/1976 | France | 73/864.82 |
| 12270 | 1/1989 | Japan | 73/864.82 |
| 967769 | 8/1964 | United Kingdom | 206/532 |

Primary Examiner—Tom Noland
Attorney, Agent, or Firm—Arthur Rosenstein; Imre (Jim) Balogh

[57] ABSTRACT

There is provided a device for placing a capsule into a container, slitting the capsule to release its content, washing the capsule and that part of the device which is in direct contact with the capsule and its content for quantitatively transferring the total content into said container for subsequent analysis.

10 Claims, 4 Drawing Sheets

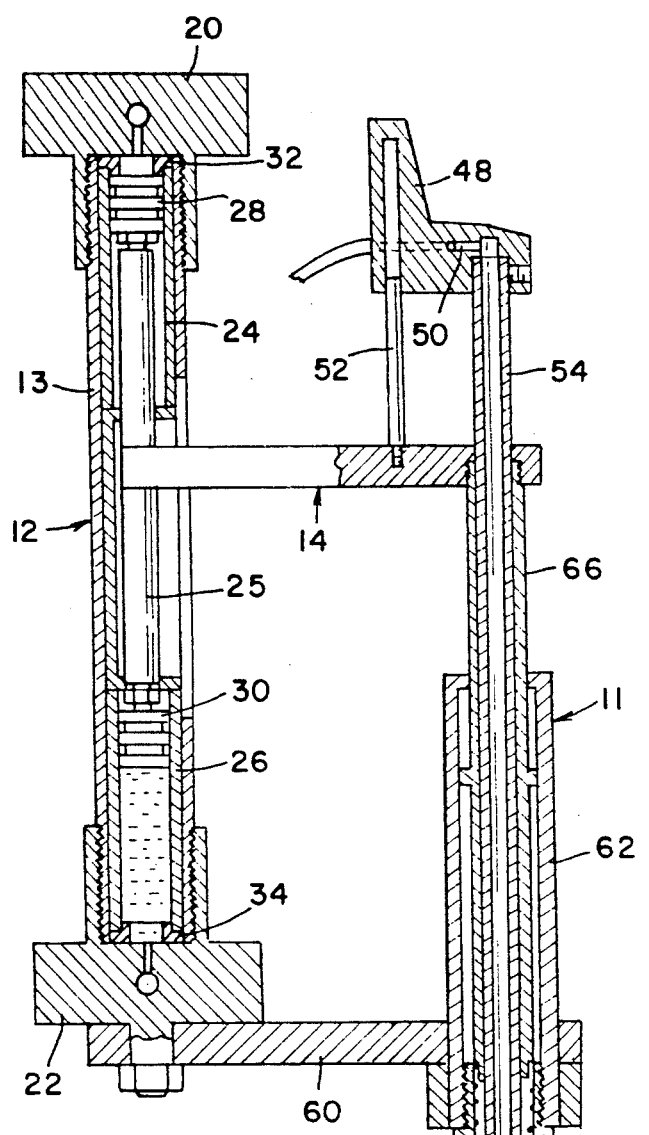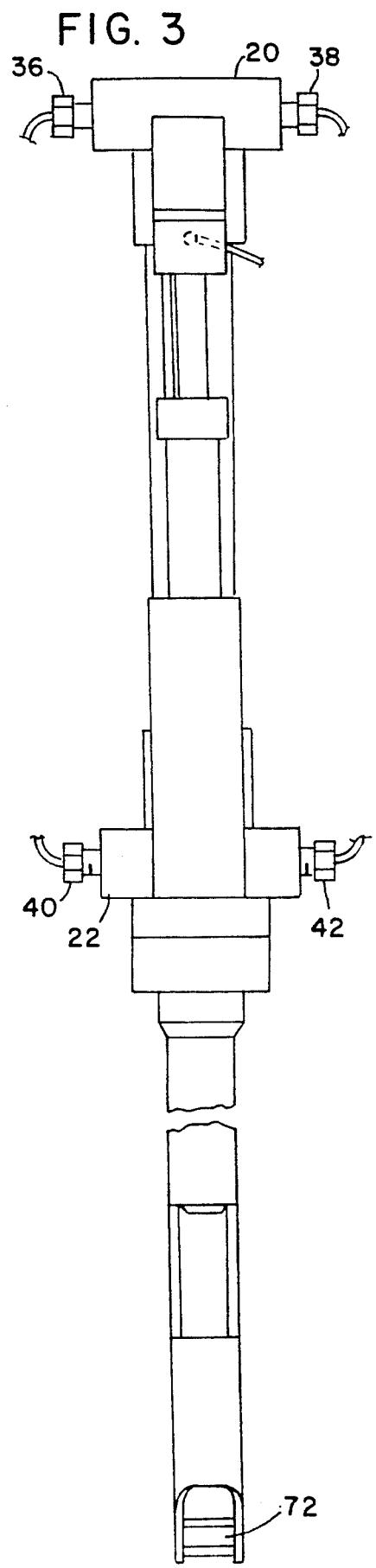
FIG. 2
FIG. 3

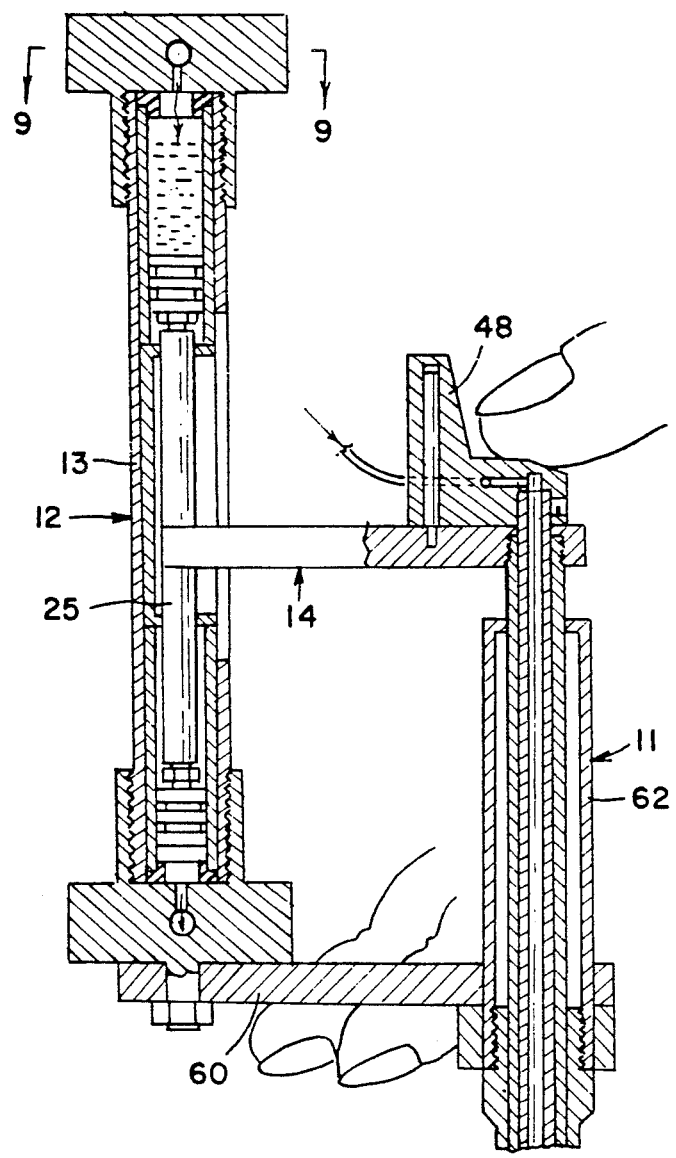
FIG. 7
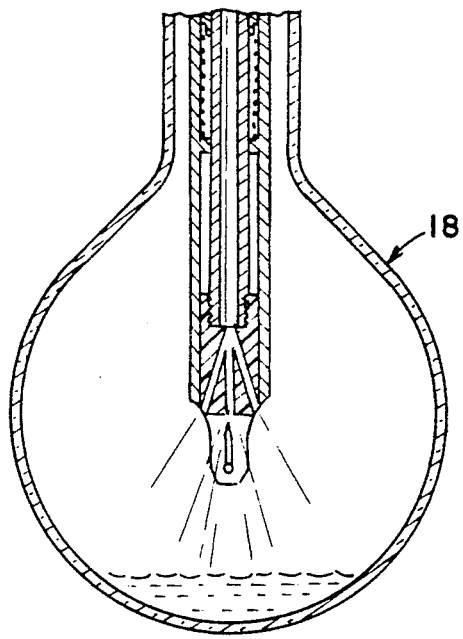

CAPSULE TRANSFER DEVICE

BACKGROUND OF THE INVENTION

1. Field of the Invention

This invention relates to a capsule transfer device of the type wherein means are provided to place a capsule into a container, slitting the capsule to release its content, washing the slitted capsule and that part of the device which is in direct contact with the capsule and content so as to quantitatively transfer all the content of the sample into the container for volumetric or other analysis.

2. Reported Developments

The prior art provides various devices for handling pharmaceutical and/or chemical samples to be analyzed in research pursuits for checking raw materials and semi-finished products during the manufacturing processes, and in the quality control of finished products. Illustrative examples of such devices are shown in the following patents.

Micheletti, U.S. Pat. No. 3,002,387, discloses a sample injector for gas chromatography capable to receive and rupture a frangible ampule and release the sample contained therein into the gas chromatography for analysis.

Cosgrove et al, U.S. Pat. No. 4,578,244, discloses an automated sampling apparatus for use in obtaining fluid samples in a dissolution testing system which is operable to receive a plurality of sampling containers and to transport them to a sampling station where fluid can be introduced into the containers and samples can be withdrawn therefrom for analysis in a suitable analytical device.

Scordato et al, U.S. Pat. No. 4,821,586, discloses an electronically programmed and operated pipette capable of aspirating and discharging a preselected volume of liquids.

In working with gelatin capsules to chemically assay their content, it is necessary to quantitatively transfer their content to a volumetric flask and fill the flask to a predetermined volume with a solvent, such as water or alcohol. Proper aliquot then can be withdrawn from the flask for further quantitative dilution and subsequent chemical analysis. Gelatin capsules are conventionally opened in an open dish or vessel, such as a beaker, by slitting with a razor blade and then transferring the capsules and their contents form the open dish into a volumetric flask. Such a process often results in the spurting of the capsules contents out of the disk and the consequent failure out of the disk and the consequent failure of the assay. In addition, holding the capsules by hand while slitting them open and then transferring their content requires the use of rinsing the hand, the capsules and the razor blade so as to quantitatively preserve the capsules' contents for analysis.

It has now been discovered that these problems can be obviated with a capsule transfer device which provides for easy handling, slitting, washing the capsule and convenient transfer of the capsule content into a volumetric flask for subsequent analysis.

SUMMARY OF THE PRESENT INVENTION

The capsule transfer device of the present invention comprises a capsule splitter to receive, transfer and split a capsule and a dual syringe pump to wash the capsule and its content into a volumetric flask for subsequent quantitative analysis. The capsule splitter comprises: a barrel having two ends, one end of which is equipped with a slot and a knife adapted to receive and split a pharmaceutical capsule; and a spring-actuated slideable shaft, positioned in said barrel, having a plunger at one end and a thumbpiece at the other end thereof, said plunger is to force the inserted capsule against the knife upon exertion of manual force on the thumbpiece. The dual spring pump comprises: a cylindrical body containing within an upper end and a lower glass cylinder which serves as syringes for containing a solvent; positioned in the cylinders are two pistons which travel the length of the cylinders and serve to draw and expel the solvent into and out of the cylinders.

The pistons are actuated by a pump actuator connected to the shaft of the capsule splitter by force exerted on the thumbpiece. The solvent is supplied from an external source through tubings to the pump and form the pump to the capsule splitter. Control of the solvent flow is accomplished by inlet and outlet check valves.

BRIEF DESCRIPTION OF THE DRAWINGS

FIG. 2 is a side sectional view of the device shown in FIG. 1;

FIG. 3 is a side plan view of the device partially broken away;

FIG. 7 is a side sectional view of the device partially broken away and inserted into a volumetric flask showing solvent spurting out of the tip of the device subsequent to the cutting of the capsule;

DESCRIPTION OF THE PREFERRED EMBODIMENT

Figure 1:
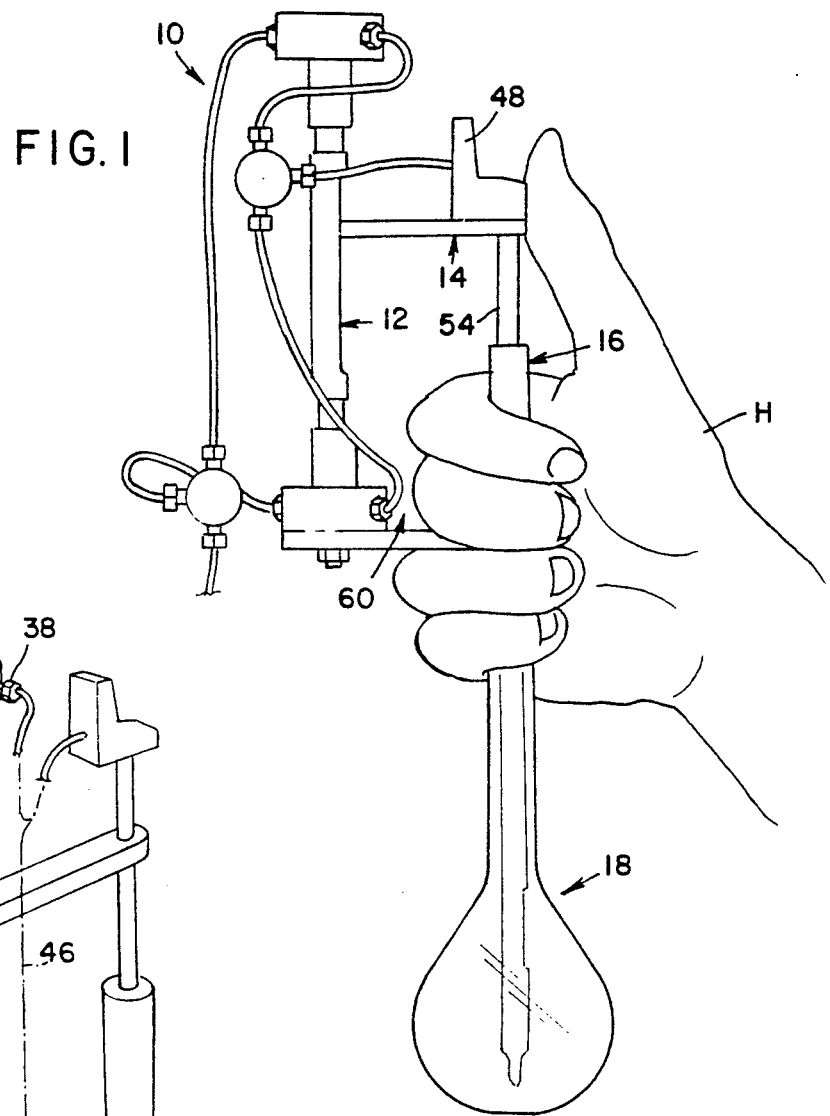
FIG. 1 is a perspective view of the capsule transfer device inserted into a volumetric flask which is hand-held during operating the device.
Figure 8:
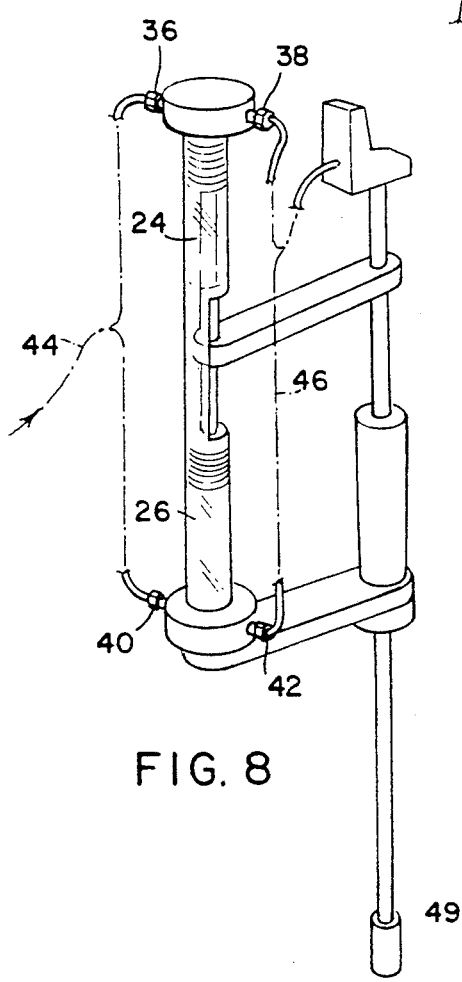
FIG. 8 is a plan view of the device of FIG. 1 showing extended thumbpiece and water-in line and water-out line.
Figure 9:
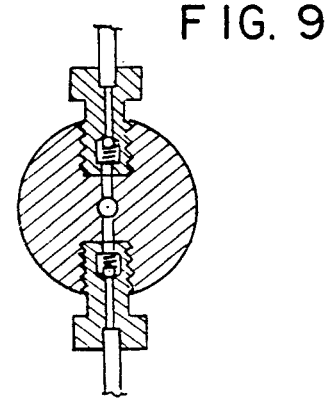
FIG. 9 is a cross-section view of the upper pump head taken along line 9—9 of FIG. 7.

The capsule transfer device of the present invention is designed to transfer one capsule directly into a volumetric flask, splitting it in half and rinsing the capsule, its content and those parts of the device which are in contact with the capsule and its content into the volumetric flask in a convenient way for subsequent quantitative analysis.

Referring to the drawings, the capsule transfer device 10 comprises: a capsule splitter 11 and dual syringe pump 12. Capsule splitter 11 comprises: a barrel 64 that is designed to fit down the neck 16 of volumetric flask 18 to introduce capsule C into said volumetric flask; at one end thereof, barrel 64 is equipped with knife 72 of the razor blade type to cut capsule C, said knife is replaceable by the removal of retaining pin 74; spaced above said knife at a distance of about the length of a capsule, slot 71 in barrel 64 is designed to receive capsule C; shaft 54 is slideably contained in barrel 64 and is equipped with thumbpiece 48 at one end and plunger 49 at the other end; spaced above barrel 64 and contiguous therewith is spring drive housing 62 which contains within spring drive 66 in a slideable relationship. Return spring 68 is positioned in barrel 64 and serves to reset the position of shaft 54 and plunger 49 which is located on said shaft. Return spring 68 also serves to actuate the inverse operation of the pump, namely, filling lower glass cylinder 26 and expelling solvent from upper glass cylinder 24 through plunger 49. Return spring 68 is maintained in position in barrel 64 by spring stop 70. Within shaft 54 there is a solvent inlet 50 continuing in water-in line 44 which is integral with rinse head 56 and water outlets 58; alignment pin 52 connects thumbpiece 48 and pump actuator 14 and serves to maintain alignment of plunger 49 with knife 72.

Dual syringe pump 12 is designed to supply rinsing solvent, such as water, on both the downstroke and the upstroke of the capsule splitter. It is connected to capsule splitter 11 with pump mount 60. Dual syringe pump 12 is actuated by the capsule splitter's thumbpiece 48, and pump actuator 14. Dual syringe pump 12 comprises cylindrical pump body 13 and two pump heads, upper pump head 20 and lower pump head 22; cylindrical pump body 13 contains upper glass cylinder 24 and lower glass cylinder 26 which serve as syringes. End cap 32, made of TEFLON or other inert material, seals upper glass cylinder 24 to upper pump head 20; while end cap 34 seals lower glass cylinder 26 to lower pump head 22. Within glass cylinder 24 is positioned piston 28 and within glass cylinder 26 is positioned piston 30. The pistons are held by connecting shaft 25 which is threaded at each end thereof to fasten the pistons and lock them onto the shaft with lock nuts. The pistons travel the length of the glass cylinders and serve to draw and expel solvent for rinsing capsule C.

The pistons 28 and 30 are actuated with pump actuator 14. Solvent-flow through the system of the capsule transfer device 10 is controlled by inlet check valves 36 and 40 and two outlet check valves 38 and 42 which are fastened to pump heads 20 and 22. The pump is primed with a solvent which will load lower glass cylinder 26 with solvent before splitting a capsule. Depressing thumbpiece 48 will cause the lower glass cylinder 26 to expel the solvent through rinse head 56 and outlets 58 of plunger 49, while upper glass cylinder 24 will be filling from a solvent reservoir (not shown). On the downstroke, inlet check valves 36 and 40 are open allowing upper glass cylinder 24 to fill from the solvent reservoir through inlet check valve 36 and lower glass cylinder 26 to expel solvent through outlet check valve 42 to plunger 49. On the return or upstroke, outlet check valve 38 and inlet check valve 40 are open, allowing lower glass cylinder 26 to fill from the solvent reservoir through inlet check valve 40 and upper glass cylinder 24 to expel solvent through outlet check valve 38 to the plunger 49. Simply put, outlet check valve 38 and inlet check valve 40 are closed on the downstroke, while inlet check valve 36 and outlet check valve 42 are closed on the upstroke. Valves 36, 38, 40 and 42 are connected by solvent TEES and TELFON tubing. Connection to plunger 49 from the outlet TEE is made by TEFLON tubing that runs through the inside of shaft 54.

The dual spring pump 12 is designed to be removable allowing pumps of different volume capacity and displacements to be used.

Figure 4:
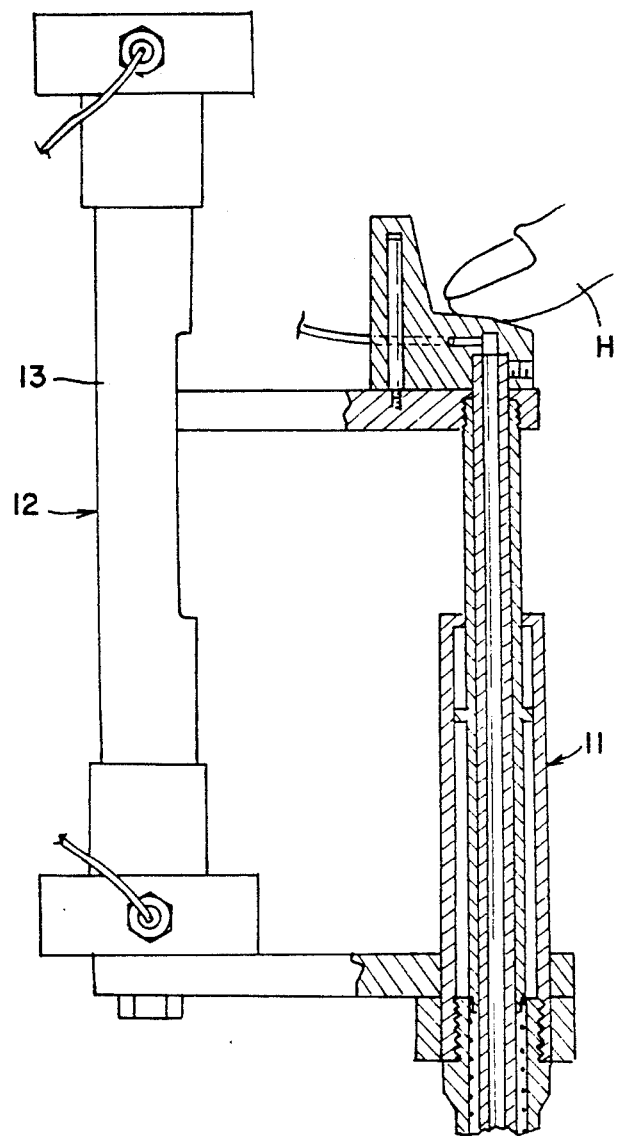
FIG. 4 is a plan view of a portion of the device showing insertion of a capsule into a capsule retaining slot.
Figure 5:
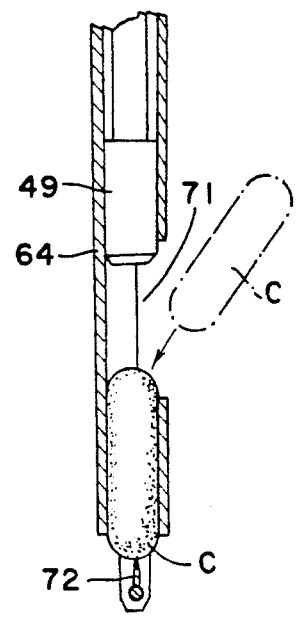
FIG. 5 is a plan view of a portion of the device showing the capsule in a position cut by the knife.
Figure 6:
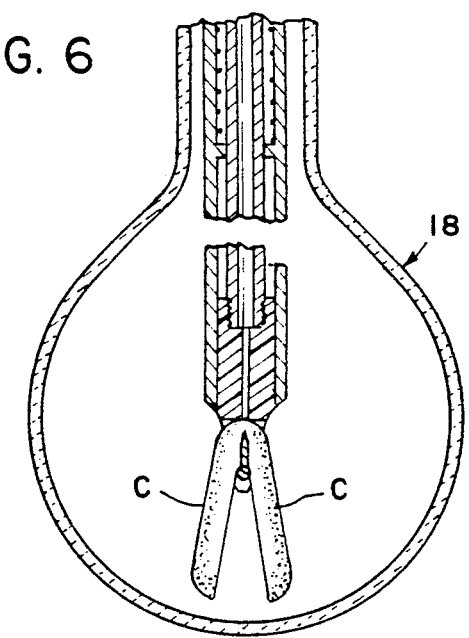
FIG. 6 is a side sectional view of the device partially broken away and inserted into a volumetric flask showing the capsule cut into two pieces.

In use, capsule C is placed into slot 71 of barrel 64 and is allowed to slide down toward knife 72 as shown in FIGS. 4 and 5. After insertion of the capsule, capsule transfer device 10 is held in one hand H and capsule splitter 11 is inserted into volumetric flask 18 as shown in FIGS. 1 and 4. Thumbpiece 48 is pressed downward until plunger 49 splits the capsule into two half-portions by forcing capsule C against knife 72. As thumbpiece 48 is pressed downward, a solvent, usually water, spurts out from rinse head 56 through outlets 58, washing/rinsing the capsule, the knife 72, the retaining pin 74 and the walls of barrel 64. Releasing thumbpiece 48 introduces more solvent into glass cylinders 24 and 26 and washing/rinsing may continue by pressing the thumbpiece as judged necessary by the operator in order to quantitatively transfer all the content of the capsule into the volumetric flask.

While the present invention has been described in connection with the preferred embodiments shown in the drawings, it is to be noted, however, that various changes and modifications are apparent to those skilled in the art.

What is claimed is:

1. A device for slitting a capsule and quantitatively transferring its content into a container comprising:
    a slitting means; and
    a washing means in cooperative relationship with said slitting means to slit and wash said capsule, said washing means comprises a dual syringe pump including tubings associated therewith through which a solvent is introduced into said device and check valves through which solvent flow is controlled.

2. A capsule transfer device for transferring a capsule into a volumetric container, splitting the capsule to release its content and washing the slitted capsule free of its content with a solvent comprising:
    a capsule splitter portion having a barrel with two ends, one of which is equipped with a slot and a knife to receive and split said capsule, and a spring-actuated slideable shaft positioned in said barrel having a plunger at one end and a thumbpiece at the other end thereof, said plunger is to force the inserted capsule against the knife upon exertion of manual force on said thumbpiece;
    a dual spring pump portion having a cylindrical body containing therewithin an upper and a lower glass cylinder for a solvent, two pistons positioned in said cylinders which travel the length of the cylinders and serve to draw and expel the solvent into and out of the cylinders;
    tubings to carry the solvent from an external source to said dual spring pump portion and from said dual spring pump portion to said capsule splitter portion; and
    check valves in said tubings to control solvent flow through said dual spring pump and said capsule splitter portions.

3. The capsule transfer device of claim 2 wherein said knife is replaceable.

4. The capsule transfer device of claim 2 further comprising a pump actuator connecting said spring-actuated slideable shaft contained in said barrel and a connecting shaft of pistons contained in said glass cylinders.

5. The capsule transfer device of claim 2 wherein said capsule splitter portion and said dual spring pump portion are simultaneously activated by a manual force exerted on said thumbpiece.

6. The capsule transfer device of claim 2 further comprising an alignment pin mounted on said pump actuator to engage said thumbpiece for maintaining alignment of said plunger with said knife.

7. A method of quantitatively transferring the content of a capsule into a volumetric container comprising the steps of:

inserting the capsule into a capsule transfer device which comprises:

a capsule splitter portion having a barrel with two ends, one of which is equipped with a slot and a knife to receive and split said capsule, and a spring-actuated slideable shaft positioned in said barrel having a plunger at one end and a thumbpiece at the other end thereof, said plunger is to force the inserted capsule against the knife upon exertion of manual force on said thumbpiece;

a dual spring pump portion having a cylindrical body containing therewithin an upper and a lower glass cylinder for a solvent, two pistons positioned in said cylinders which travel the length of the cylinders and serve to draw and expel the solvent into and out of the cylinders;

tubings to carry the solvent from an external source to said dual spring pump portion and from said dual spring pump portion to said capsule splitter portion; and check valves in said tubings to control solvent flow through said dual spring pump and said capsule splitter portions; and manually exerting pressure on said thumbpiece to depress the same at least once to split and wash the capsule and its content into said volumetric container.

8. The method of claim 7 further comprising the step of: washing said knife and said barrel when washing said capsule so that all the content of the capsule is quantitatively transferred to said volumetric container.

9. The method of claim 7 further comprising the step of releasing said thumbpiece to introduce more solvent into said glass cylinders to repeat washing said capsule and its content.

10. The method of claim 7 wherein said capsule splitter portion and said dual spring pump portion of the capsule transfer device are simultaneously activated by a manual force exerted on said thumbpiece.

* * * * *